United States Patent
Furo et al.

(10) Patent No.: US 9,809,697 B2
(45) Date of Patent: Nov. 7, 2017

(54) CROSSLINKING AGENT, CROSSLINKED POLYMER, AND COMPOUND

(71) Applicant: THE NIPPON SYNTHETIC CHEMICAL INDUSTRY CO., LTD., Osaka (JP)

(72) Inventors: Chizuko Furo, Osaka (JP); Taiji Kanda, Osaka (JP); Shusaku Mandai, Osaka (JP); Takeshi Kuroda, Osaka (JP)

(73) Assignee: THE NIPPON SYNTHETIC CHEMICAL INDUSTRY CO., LTD., Osaka (JP)

( * ) Notice: Subject to any disclaimer, the term of this patent is extended or adjusted under 35 U.S.C. 154(b) by 0 days.

(21) Appl. No.: 15/027,773

(22) PCT Filed: Oct. 8, 2014

(86) PCT No.: PCT/JP2014/077002
§ 371 (c)(1),
(2) Date: Apr. 7, 2016

(87) PCT Pub. No.: WO2015/053342
PCT Pub. Date: Apr. 16, 2015

(65) Prior Publication Data
US 2016/0237245 A1     Aug. 18, 2016

(30) Foreign Application Priority Data
Oct. 9, 2013    (JP) ................. 2013-211979

(51) Int. Cl.
*C08K 5/25*     (2006.01)
*C07C 243/28*   (2006.01)
*C08L 101/06*   (2006.01)

(52) U.S. Cl.
CPC .............. *C08K 5/25* (2013.01); *C07C 243/28* (2013.01); *C08L 101/06* (2013.01)

(58) Field of Classification Search
None
See application file for complete search history.

(56) References Cited

U.S. PATENT DOCUMENTS 4,524,006 A    6/1985 Sandel

FOREIGN PATENT DOCUMENTS

| JP | S52-033948 A | 3/1977 |
| JP | 2003-011489 A | 1/2003 |
| JP | 2004-249528 A | 9/2004 |
| JP | 2006-316142 A | 11/2006 |

OTHER PUBLICATIONS

Hulme et al., "An Efficient Synthesis of Substituted Hydrazides", Synlett, 2005, pp. 1571-1574 (Jul. 2005).*
Cates, Lindley A., Phosphorus-nitrogen compounds. VII. Urea, aziridinecarboxamide, and semicarbazide derivatives, Univ. of Houston, Houston, TX, USA, Journal of Medicinal Chemistry (1967), 10(5), 924-7.*
Kalikhman et al., "Z, E-isomerism of aromatic acid x-methlhydrazides", Izvestiya Akademii Nauk SSSR, Seriya Khimicheskaya, 1981, pp. 1268-1271, (6).
Sarapulova et al., "IR- and UV-spectra of x- and B-methylhydrazides of aromatic acids", Izvestiya Akademii Nauk SSSR, Seriya Khimicheskaya, 1982, pp. 1405-1408, (6).
Terletskaya et al., "Chemiluminescence of some acyclic hydrazides in chlorine oxidation", Ukrainskii Khimicheskii Zhurnal, 1979, pp. 1227-1233, 45 (12).
Volkova et al., "Dimethyldihydrazides of phthalic acids", Izvestiya Sibirskogo Otdeleniya Akademii Nauk SSSR, Seriya Khimicheskikh Nauk, 1978, pp. 146-148, (6).
Shevchenko et al., "Reaction of monoalkylhydrazines with dilsocyanates", Xhurnal Organicheskoi Khimii, 1975, pp. 1198-1201, 11 (6).
Goldin et al., "Synthesis of disilylsemicarbazides", Zhurnal Obshchei Khimii, 1969, pp. 2313-2315, 39 (10).
International Search Report issued with respect to application No. PCT/JP2014/077002, dated Jan. 13, 2015.
International Preliminary Report on Patentability issued with respect to application No. PCT/JP2014/077002, dated Apr. 12, 2016.
European Search Report issued with respect to Application No. 14853110.6, dated May 22, 2017.

* cited by examiner

*Primary Examiner* — Jeffrey Mullis
(74) *Attorney, Agent, or Firm* — Greenblum & Bernstein, P.L.C.

(57) ABSTRACT

An object of the invention is to provide a crosslinking agent with which a crosslinked polymer that suffers little coloring with the lapse of time and shows excellent viscosity stability is obtained. The crosslinking agent of the invention includes a compound which contains two or more alkylhydrazide groups represented by the following general formula (1).

[Chem. 1]

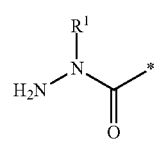

(1)

(In formula (1), $R^1$ represents an alkyl group having 1-10 carbon atoms, and symbol * is a linking bond.)

7 Claims, 1 Drawing Sheet

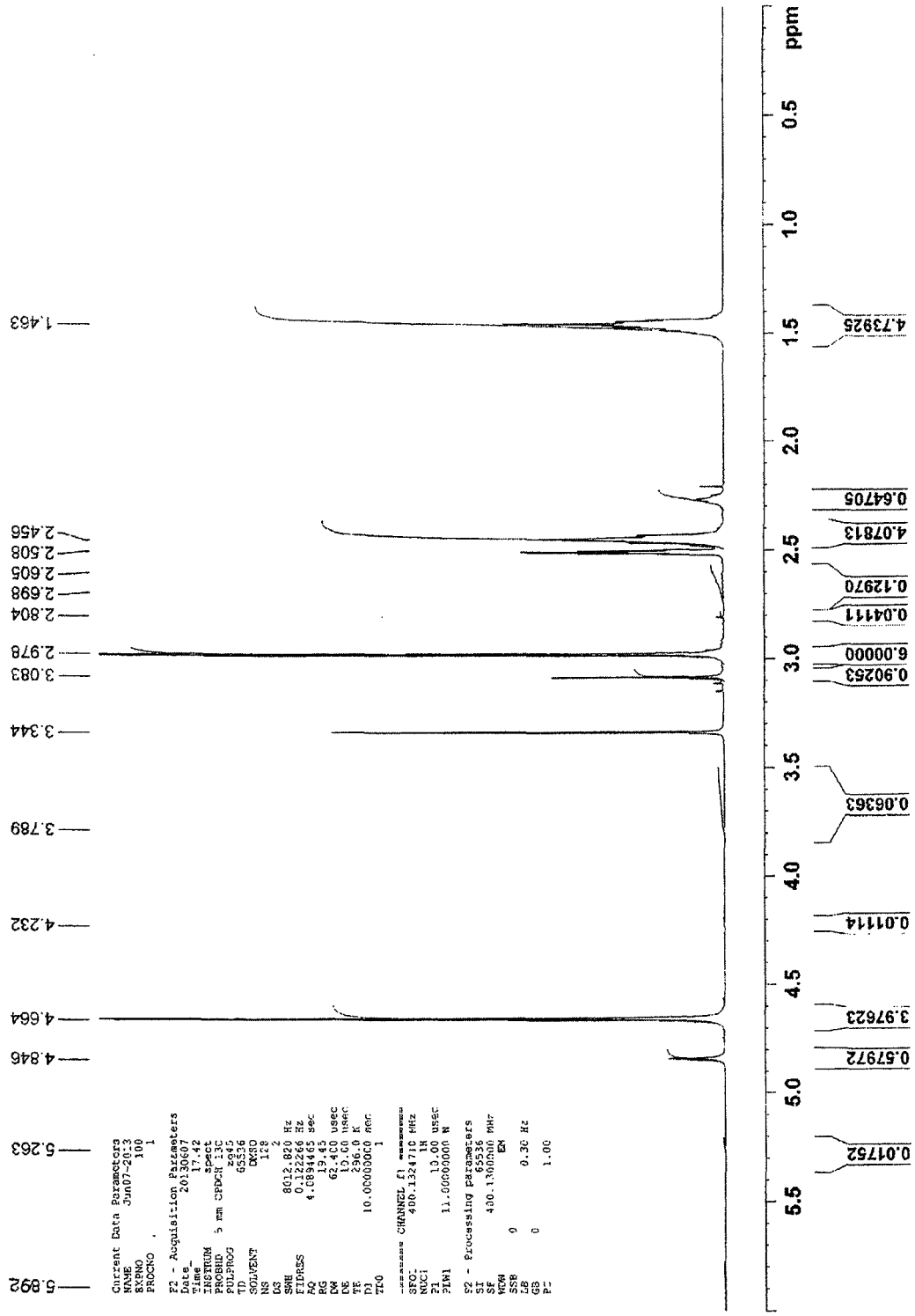

CROSSLINKING AGENT, CROSSLINKED POLYMER, AND COMPOUND

TECHNICAL FIELD

The present invention relates to a crosslinking agent, a crosslinked polymer obtained by crosslinking with the crosslinking agent, and a novel compound.

BACKGROUND ART

A crosslinking agent is an agent which mainly serves to chemically bond molecules of a polymeric compound to each other. The crosslinked structure formed with a crosslinking agent generally has improved properties, e.g., strength, heat resistance, and solvent resistance, as compared with an uncrosslinked polymeric compound.

Although various crosslinking agents have been proposed, compounds containing a hydrazide group have been proposed as crosslinking agents which are usable in an aqueous system without using any organic solvent, due to the recent increasing concern about environmental issues. For example, patent document 1 discloses a hydrazide-group-containing copolymer having a specific structural unit. Since compounds containing a hydrazide group are suitable for use in applications where a relatively high crosslinking rate is desired, patent document 2 discloses a feature wherein a compound containing a hydrazide group is used as an adhesive in the thermal recording layer and/or protective layer of a thermal recording medium.

A crosslinked polymer crosslinked with a crosslinking agent has a three-dimensional network structure formed therein. This crosslinked polymer is obtained by a crosslinking reaction between a linear polymer having reactive functional groups in the side chains or main chain thereof and a crosslinking agent.

As such linear polymer, various polymers are being investigated, such as acrylic resins, urethane-based resins, epoxy-based resins, and polyvinyl alcohol-based resins. Such linear polymers in which carbonyl groups have been introduced into the side chains or main chain are in extensive use because of the high reactivity thereof.

Of these, polyvinyl alcohol-based resins (hereinafter, polyvinyl alcohol is abbreviated to PVA), which are water-soluble resins, can be made to have water resistance by crosslinking, and are among the resins which are practically important from the standpoint of forming crosslinked polymers therefrom.

In the case of such PVA-based resins, it is preferable that a modified PVA-based resin into which carbonyl groups have been introduced should be used, from the standpoints of heightening the efficiency of crosslinking and forming a strong crosslinked structure. Examples of such modified PVA-based resins include an acetoacetyl group-containing PVA-based resin (hereinafter referred to as AA-modified PVA-based resin), a PVA-based resin containing a diacetone acrylamide structural unit (hereinafter referred to as DAAA-PVA-based resin), and a carboxylic-acid-modified PVA-based resin.

As stated above, compounds containing a hydrazide group are in extensive use as crosslinking agents for linear polymers, in particular, polymers having carbonyl groups, for example AA-modified PVA-based resins and DAAA-PVA-based resins. However, the crosslinked polymers obtained by crosslinking with compounds containing a hydrazide group have had a problem in that the crosslinked polymers take a color with the lapse of time depending on the storage environment. In order to overcome this problem, various investigations have been made so far.

Examples of such investigations include to incorporate a reducing agent as described in patent document 3.

PRIOR-ART DOCUMENTS

Patent Documents

Patent Document 1: JP-A-2006-316142
Patent Document 2: JP-A-2004-249528
Patent Document 3: JP-A-2009-280754

SUMMARY OF THE INVENTION

Problem that the Invention is to Solve

However, in the case of incorporating a reducing agent or the like, there is a possibility that the original properties of the crosslinking agent or of the compound to be crosslinked might be impaired, and the reducing agent or the like cannot hence be used in a large amount. There has hence been a problem in that an effective means for inhibiting the coloring has not yet been established.

Namely, an object of the invention is to provide a crosslinking agent for use in forming crosslinked polymers which includes an alkylhydrazide-group-containing compound and with which crosslinked polymers that suffer little coloring with the lapse of time and have excellent viscosity stability are obtained.

Means for Solving the Problem

The present inventors diligently made investigations under these circumstances and, as a result, have discovered that the object of the invention is accomplished with a crosslinking agent containing two or more specific alkylhydrazide groups. The invention has been thus completed.

The present invention includes the following configurations [1] to [8].

[1] A crosslinking agent comprising a compound which contains two or more alkylhydrazide groups represented by the following general formula (1):

[Chem. 1]

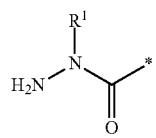

(1)

(In formula (1), $R^1$ represents an alkyl group having 1-10 carbon atoms, and symbol * is a linking bond.)

[2] The crosslinking agent according to [1], wherein the compound has a solubility in 100 g of water of 50-500 g at 23° C.

[3] The crosslinking agent according to [1] or [2], wherein the compound has a molecular weight of 150-3,000.

[4] The crosslinking agent according to [1], wherein the compound is a dicarboxylic acid bis(1-alkylhydrazide) compound represented by the following general formula (1a):

[Chem. 2]

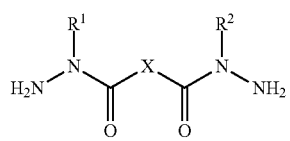

(1a)

(In formula (1a), $R^1$ and $R^2$ each independently represent an alkyl group having 1-10 carbon atoms, and X represents a single bond or an alkylene chain having 1-10 carbon atoms.)

[5] The crosslinking agent according to any one of [1] to [4], which is for use in crosslinking a polymer having carbonyl groups.

[6] The crosslinking agent according to [5], wherein the polymer is a polyvinyl alcohol-based resin.

[7] A crosslinked polymer produced by crosslinking a polyvinyl alcohol-based resin with the crosslinking agent according to any one of [1] to [6].

[8] A compound which contains two or more alkylhydrazide groups represented by the following general formula (1):

[Chem. 3]

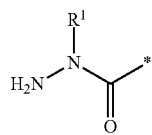

(1)

(In formula (1), $R^1$ represents an alkyl group having 1-10 carbon atoms, and an symbol * is a linking bond.)

This compound functions as a crosslinking agent for linear polymers by a mechanism in which the alkylhydrazide groups represented by general formula (1) within the molecule react with functional groups, e.g., carbonyl groups, of the linear polymers.

Although the crosslinking agent of the invention includes, as an effective component, a compound containing at least two alkylhydrazide groups represented by general formula (1), the term "effective component" means that this compound functions substantially as a crosslinking agent.

Effects of the Invention

The crosslinking agent of the invention provides crosslinked polymers obtained therewith which are inhibited from suffering coloring with the lapse of time and have excellent viscosity stability.

The crosslinking agent of the invention is useful as a crosslinking agent for linear polymers, especially, PVA-based resins having carbonyl groups, in particular, acetoacetyl-containing PVA-based resins (AA-modified PVA-based resins) or PVA-based resins containing a diacetone acrylamide structural unit (DAAA-PVA-based resins). This crosslinking agent not only has excellent reactivity in crosslinking but also has a feature wherein mixed aqueous solutions containing both the crosslinking agent and any of those PVA-based resins have excellent viscosity stability and a long pot life. In addition, the crosslinked polymers obtained have the feature of being highly inhibited from taking a color with the lapse of time.

Meanwhile, adipic acid dihydrazide (ADH) is known as a crosslinking agent for AA-modified PVA-based resins or DAAA-PVA-based resins. However, the crosslinked polymers obtained by crosslinking AA-modified PVA-based resins or DAAA-PVA-based resins with ADH take a color with the lapse of time. In contrast, in cases when the crosslinking agent of the invention is used, crosslinked polymers which are highly inhibited from taking a color with the lapse of time are obtained.

It has conventionally been thought that in some of a crosslinked structure formed by the crosslinking of carbonyl groups with ADH, the NH-group nitrogen derived from the hydrazine compound nucleophilically attacks the carbonyl carbon derived from an acetoacetic acid ester group and subsequently cleaves the ester group to form a vinyl alcohol structure on the PVA-based resin side and yield a compound having a pyrazolone ring, which is causative of coloring, as shown by the following scheme.

[Chem. 4]

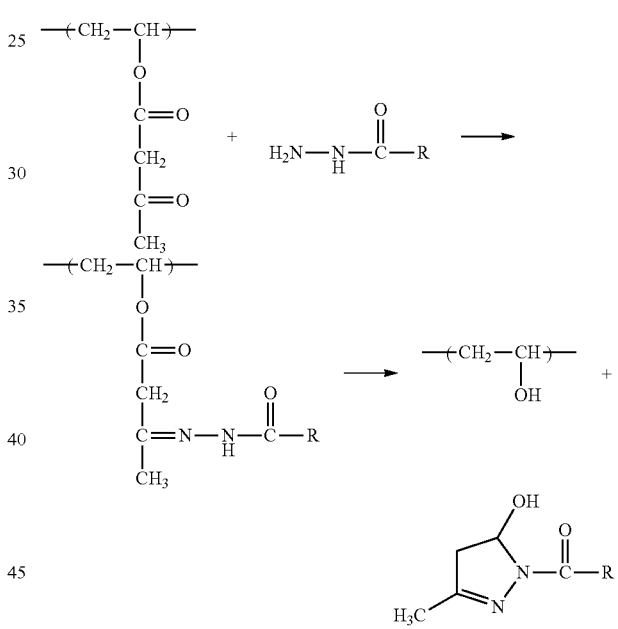

In the crosslinking agent of the invention, the hydrogen atom of the NH group of each hydrazide group has been replaced with an alkyl group having 1-10 carbon atoms. It is presumed that due to the replacement, the nitrogen atom shows reduced nucleophilicity and the crosslinking agent does not yield a pyrazolone ring compound such as that shown above. Thus, prevention of coloring has become possible.

BRIEF DESCRIPTION OF THE DRAWING

FIG. 1 is a $^1$H-NMR spectrum of a crosslinking agent {compound of general formula (4)}.

MODES FOR CARRYING OUT THE INVENTION

The following explanations on constituent elements are for embodiments (representative embodiments) of the invention, and the invention should not be construed as being limited to the following embodiments.

The present invention will be explained below in detail.

[Compound Having Alkylhydrazide Groups]

First, the compound having alkylhydrazide groups which is to be contained as an effective component in the crosslinking agent of the invention is explained.

This compound having alkylhydrazide groups is a compound which has therein two or more alkylhydrazide groups represented by the following general formula (1).

[Chem. 5]

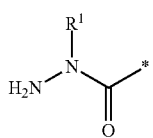

(1)

In formula (1), $R^1$ represents an alkyl group having 1-10 carbon atoms. This alkyl group may have one or more substituents so long as the effects of the invention are not lessened thereby. Examples of the substituents include halogen group, hydroxyl group, ester groups, carboxy group, and sulfa group. The number of carbon atoms of $R^1$ is preferably 1 to 5, more preferably 1 to 3. Symbol * indicates a linking bond.

Two or more such alkylhydrazide groups are usually contained in the compound. The number thereof is preferably 2 to 4, more preferably 2 or 3.

The crosslinking agent of the invention has an alkylhydrazide group equivalent [(number of alkylhydrazide groups)/(overall molecular weight)] of usually 0.001 or higher, preferably 0.005 to 0.1, especially preferably 0.01 to 0.09. In case where the amount of the groups is too large, there is a tendency that the compound itself has reduced stability. In case where the amount thereof is too small, the crosslinking performance tends to decrease.

It is preferable that the compound to be used should be one which dissolves in 100 g of 23° C. water in an amount (solubility) of usually 50-500 g, preferably 70-300 g, more preferably 100-200 g.

The molecular weight of the compound containing alkylhydrazide groups is usually 150-3,000, preferably 180-1,000, more preferably 200-700. Too high molecular weights thereof tend to result in a decrease in water solubility, while too low molecular weights thereof tend to result in a decrease in stability.

This compound may have an average particle diameter of usually 0.01-3,000 µm, preferably 0.1-1,000 µm, especially preferably 1-100 µm. As a method for determining the particle diameter, a laser diffraction method may be used.

Preferred embodiments of the compound containing alkylhydrazide groups include a dicarboxylic acid bis(1-alkylhydrazide) compound represented by the following general formula (1a).

[Chem. 6]

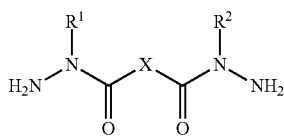

(1a)

In formula (1a), $R^1$ and $R^2$ each independently represent an alkyl group having 1-10 carbon atoms, and the two may be the same or different. The alkyl group may have one or more substituents as in general formula (1). The number of carbon atoms of $R^1$ and that of $R^2$ each preferably is 1-5, more preferably 1-3.

In case where the number of carbon atoms thereof is too large, this compound tends to have reduced water solubility.

X represents a single bond or an alkylene chain which has 1-10 carbon atoms and may have one or more substituents. X is preferably an alkylene chain having 1-6 carbon atoms, more preferably an alkylene chain having 2-5 carbon atoms, even more preferably an alkylene chain having 3 or 4 carbon atoms.

In case where the number of carbon atoms thereof is too large, this compound tends to have reduced water solubility.

Examples of the compound having two or more alkylhydrazide groups according to the invention include a compound represented by the following general formula (1b), as a compound which has two alkylhydrazide groups so that the carbonyl group is shared by the two groups.

[Chem. 7]

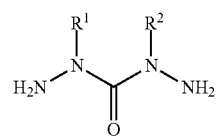

(1b)

In formula (1b), $R^1$ and $R^2$ each independently represent an alkyl group having 1-10 carbon atoms, and the two may be the same or different. The alkyl group may have one or more substituents as in general formula (1). The number of carbon atoms of $R^1$ and that of $R^2$ each preferably is 1-5, more preferably 1-3.

The carbonyl group does not participate in crosslinking reactions, and it is presumed that the compound of general formula (1b), in which the carbonyl group is shared, behaves like the compound of the invention which contains unshared carbonyl groups.

Processes for producing the compound having alkylhydrazide groups are not particularly limited. Examples thereof include a process in which a carboxylic acid compound is reacted with thionyl chloride to obtain a chloride of the carboxylic acid and this carboxylic acid chloride is then reacted with an alkylhydrazine to obtain the desired compound.

[Crosslinking Agent]

The crosslinking agent of the invention includes the compound containing alkylhydrazide groups. The crosslinking agent of the invention is suitable for use in crosslinking polymers having functional groups such as carbonyl groups, epoxy groups or isocyanate groups. The crosslinking agent is more suitable for the crosslinking of polymers having carbonyl groups among those.

There is a possibility that the crosslinking agent of the invention might contain some of the starting materials used for the production, impurities contained in the starting materials, by-products yielded in the production, etc. For example, there are cases where the crosslinking agent contains an alkylhydrazine, e.g., methylhydrazine, the following compounds which are by-products, etc.

[Chem. 8]

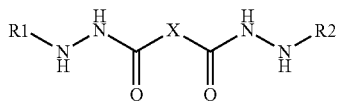

(In the formula, R1 and R2 each independently represent an alkyl group which has 1-10 carbon atoms and may have one or more substituents, and the two may be the same or different. X represents a single bond or an alkylene chain which has 1-10 carbon atoms and may have one or more substituents.)

[Crosslinked Polymer]

Next, the crosslinked polymer of the invention, is explained. The crosslinked polymer of the invention is a polymer which has been reacted with the crosslinking agent of the invention to form a crosslinked structure and which has thus undergone intermolecular crosslinking.

Linear polymers to be used for producing the crosslinked polymer are not particularly limited so long as the linear polymers have functional groups capable of reacting with the alkylhydrazide groups. Examples of such functional groups include carbonyl, epoxy, and isocyanate groups. Preferred of these is carbonyl group. Specifically, an acetoacetyl group and a diacetone acrylamide structural unit are a preferred functional group and a preferred structural unit from the standpoint of the excellent reactivity thereof with the crosslinking agent of the invention.

Polymers having functional groups such as acetoacetyl groups in the side chains and polymers having diacetone acrylamide structural units are not particularly limited so long as these polymers are linear polymers. Examples thereof include polyolefin-based resins such as polyethylene and polypropylene, polyester-based resins such as polyethylene terephthalate, polybutylene terephthalate, and polyethylene naphthalate, polyamide-based resins such as nylon-6, nylon-11, nylon-12, and nylon-66, polyvinyl-based resins such as polyvinyl chloride, polyvinyl acetate, polyvinyl alcohol, polyacrylic acid, and polymethyl methacrylate, polydiolefin-based resins such as polybutadiene and polyisoprene, polyether-based resins such as polyacetal and polyethylene oxide, polyurethane-based resins, polycarbonate-based resins, polyimide-based resins, formaldehyde-based resins, and polyol-based resins. Of these, polyvinyl alcohol-based resin are suitable. These linear polymers may be either in a straight-chain form or a branched form.

It is preferable that the crosslinking agent of the invention to be used should be a water-soluble one. The water soluble crosslinking agent can be mixed in an aqueous medium with a polymer to be crosslinked, in the case where the polymer is water-soluble. Although the following explanation is given on the case Where a PVA-based resin is used as the water-soluble resin, the polymer should not be construed as being limited to PVA-based resins.

Examples of methods for the mixing include (i) a method in which both the crosslinking agent and a PVA-based resin are added to water and dissolved therein, (ii) a method in which the crosslinking agent is added to and mixed with an aqueous solution of a PVA-based resin, and (iii) a method in which a solution of a PVA-based resin and a solution of the crosslinking agent which have been separately dissolved beforehand are mixed with each other.

Of these, method (iii) is preferred.

It is preferable that the concentration of the aqueous solution of a PVA-based resin, which is to be used in the method for preparing an aqueous resin composition solution, should be 0.05-40% by weight, preferably 1-30% by weight, especially 1-20% by weight. Too high concentrations of the aqueous solution of a PVA-based resin are undesirable since there are cases where such a solution has so high a viscosity that application thereof to substrates or use thereof in various steps is difficult. Meanwhile, too low concentrations thereof are undesirable because use of such a solution results in an insufficient resin amount or necessitates a prolonged drying period.

Other known crosslinking agents may be incorporated into the aqueous solution so long as the features of the invention are not adversely affected thereby. Examples of such usable crosslinking agents include compounds of polyvalent metals, such as ones represented by water-soluble titanium compounds, water-soluble zirconium compounds, or water-soluble aluminum compounds, boron compounds such as boric, acid and borax, amine compounds (diamine compounds, polyamine compounds, polyallylamine, etc.), hydrazine compounds (e.g., adipoyldihydrazide), high-molecular-weight hydrazides (polyaminoacrylamide manufactured by Otsuka Chemical Co., Ltd.), silane compounds, methylol-group-containing compounds (methylolmelamine, etc.), aldehyde-group-containing compounds (glyoxal, dimethoxyethanal, glutaraldehyde, glyoxalic acid and derivatives thereof such as hemiacetal forms and acetal forms, etc.), epoxy compounds, thiol compounds, isocyanate compounds, polyisocyanate compounds ("Hydran Assister C1", manufactured by DIC Corp., etc.), blocked isocyanate compounds (ketoxime-blocked ones, phenol-blocked ones, etc.), water-soluble or water-dispersible epoxy resins or compounds (polyethylene glycol) diglycidyl ether, polypropylene glycol diglycidyl ether, polytetramethylene glycol diglycidyl ether, neopentyl glycol diglycidyl ether, diglycerin diglycidyl ether, ethylene glycol diglycidyl ether, propylene glycol diglycidyl ether, 1,4-butanediol diglycidyl ether, 1,6-hexanediol diglycidyl ether, bisphenol A diglycidyl ether, bisphenol F diglycidyl ether, resorcin diglycidyl ether, glycerin triglycidyl ether, trimethylolpropane triglycidyl ether, pentaerythritol polyglycidyl ethers, sorbitol polyglycidyl ethers, sorbitan polyglycidyl ethers, polyglycerol polyglycidyl ethers, etc.), water-soluble or water-dispersible oxetane resins or compounds, polyamide-amine/epichlorohydrin resins, and polyethylene imine. These crosslinking agents may be used either alone or in combination of two or more thereof.

Additives such as a defoamer, fungicide, antiseptic, and leveling agent and other ingredients including various emulsions, polyester-based ionomer type urethane resins (e.g., "Hydran AP-20" and "Hydran APX-101H", both manufactured by DIC Corp.), various polymer dispersions represented by polyurethane-based dispersions and polyester-based dispersions, water-soluble resins such as polyhydroxyethyl methacrylate, polyhydroxyethyl acrylate, and polyacrylic acid, compounds having a glycidyloxy group, and colloids of metals such as aluminum (e.g., "Alumina Sol-10A", manufactured by Kawaken Fine Chemicals Co., Ltd.) may be incorporated into the aqueous solution so long as the features of the invention are not adversely affected thereby.

The pH of this aqueous resin composition solution is usually 2-10, preferably 3-10, more preferably 4-9. When the pH thereof is too high, there are cases where use of this aqueous resin composition solution results in, for example, the corrosion of the apparatus used for applying the solution and it becomes necessary to take a measure against such troubles. Conversely, in case where the pH thereof is too low, this aqueous resin composition solution is prone to increase in viscosity and tends to have a shortened pot life.

The thus-prepared aqueous resin composition solution according to the invention may be used in various applications by known methods, e.g., coating, casting, and immersion. Thereafter, a crosslinking reaction between the PVA-based resin and the crosslinking agent proceeds to give a crosslinked structure. Simultaneously with or after the formation of the crosslinked structure, the solution applied is dried to remove the water.

Alternatively, use may be made of a method in which an aqueous solution containing either the PVA-based resin or the crosslinking agent is applied, cast, or immersed in advance and an aqueous mixture solution containing the remainder is applied, cast, or immersed thereafter. In this case, a crosslinking reaction proceeds when the PVA-based resin has come into contact with the crosslinking agent, thereby obtaining a crosslinked structure. The mixture is dried to remove the water as in the case described above.

According to need, the crosslinked structure is dried with heating or dried at a low to ordinary temperature. Thus, the purpose of water resistance to the PVA-based resin can be accomplished. Conditions of the drying are not particularly limited, and may be suitably selected according to modes of use. However, it is preferred to use temperature conditions of usually 5-150° C., preferably 30-150° C., especially 50-150° C., and a drying time of 0.1-60 minutes, preferably 0.1-30 minutes, especially 0.2-20 minutes.

Although the heat resistance and solvent resistance of linear polymers can be improved by crosslinking the linear polymers, the effect of the crosslinking is highly remarkable in the case of, in particular, PVA-based resins because these resins in themselves are water-soluble and are made to have improved water resistance by conversion into crosslinked polymers.

The crosslinked polymer obtained by crosslinking a PVA-based resin using the crosslinking agent of the invention is useful in various applications where water resistance is required. In particular, the crosslinked polymer is suitable for various adhesive applications, binder applications, coating material applications, etc.

The crosslinked polymer is usable in applications where water resistance is required, besides the applications shown above. Examples thereof include the following.

(1) Paper Processing Agents

The undercoat layers or back coat layers of various kinds of converted paper; the color development layers or intermediate layers of sublimation type thermal recording media; binders for inorganic fine particles for void type ink-jet recording media; the ink-receiving layers of swelling type ink-jet recording media; clear coating materials for paper; pigment binders for coated paper; pigment binders for electrophotographic recording media; surface coating materials or pigment binders for release paper; the heat-resistant protective layers of thermal transfer recording media; etc.

(2) Adhesives

Two-pack type adhesives, honeymoon type adhesives, tacky adhesives, resoluble adhesives, binders for nonwoven fabric, binders for building materials (e.g., gypsum boards and fiberboards), binders for granulation of various powders, pressure-sensitive adhesives, the binders of anionic coating materials, etc.

(3) Aqueous Gels

Supports for wastewater treatment, water-holding materials, cold-reserving materials, bioreactors, fragrances, soil improvers, organ models, artificial joints, artificial muscles, artificial baits, etc.

(4) Coating Materials

Fiber processing agents, leather finishing agents, coating materials, antifogging agents, metal corrosion inhibitors, gloss agents for galvanized iron, antistatic agent, electroconductive materials, tentative coating materials, tentative protective films, etc.

(5) Films, Membranes, and Fibers

Electrolyte membranes, films for packaging, nonwoven fabric for separators, nonwoven fabric for filters for organic solvents, nonwoven fabric for sound absorbing materials, nonwoven fabric for packaging, nonwoven nanofiber fabric, etc.

(6) Thickeners

Thickeners for excavation fluids, etc.

[AA-Modified PVA-Based Resin and Crosslinked Polymer Therefrom]

Next, a crosslinked polymer obtained from the crosslinking agent of the invention and an AA-modified PVA-based resin is explained, this crosslinked polymer being a preferred mode of use of the crosslinking agent of the invention.

The AA-modified PVA-based resin to be used in the invention is a PVA-based resin which has acetoacetyl groups in the side chains thereof.

Processes for producing the AA-modified PVA-based resin are not particularly limited. Examples thereof include a method in which a PVA-based resin is reacted with diketene, a method in which a PVA-based resin is reacted with an acetoacetic acid ester to conduct transesterification, and a method in which a copolymer of vinyl acetate with vinyl acetoacetate is saponified. However, it is preferred to produce an AA-modified PVA-based resin by the method in which a PVA-based resin is reacted with diketene since the production steps are simple and the AA-modified PVA-based resin obtained has high quality. This method is explained below.

The PVA-based resin to be used as a starting material generally is either a product of saponification of a polymer of one or more vinyl ester monomers or a derivative of the saponification product. Examples of the vinyl ester monomers include vinyl formate, vinyl acetate, vinyl propionate, vinyl valerate, vinyl butyrate, vinyl isobutyrate, vinyl pivalate, vinyl caprate, vinyl laurate, vinyl stearate, vinyl benzoate, and Vinyl Versatate. From the standpoint of profitability, it is preferred to use vinyl acetate.

It is also possible to use, for example, a product of saponification of a copolymer of a vinyl ester monomer with a monomer having copolymerizability with the vinyl ester monomer. Examples of the comonomer include olefins such as ethylene, propylene, isobutylene, α-octene, α-dodecene, and α-octadecene, hydroxyl-containing α-olefins such as 3-buten-1-ol, 4-penten-1-ol, 5-hexen-1-ol, and 3,4-dihydroxy-1-butene and derivatives thereof such as acylation products, unsaturated acids such as acrylic acid, methacrylic acid, crotonic acid, maleic acid, maleic anhydride, itaconic acid, and undecylenic acid and salts, monoesters, or dialkyl esters thereof, nitriles such as acrylonitrile and methacrylonitrile, amides such as diacetone acrylamide, acrylamide, and methacrylamide, olefinsulfonic acids such as ethylenesulfonic acid, allylsulfonic acid, and methallylsulfonic acid and salts thereof, alkylvinyl ethers, vinyl compounds such as dimethylallyl vinyl ketone, N-vinylpyrrolidone, vinyl chloride, vinylethylene carbonate, 2,2-dialkyl-4-vinyl-1,3-dioxolanes, and glycerin monoallyl ether, substituted vinyl acetates such as isopropenyl acetate and 1-methoxyvinyl acetate, vinylidene chloride, 1,4-diacetoxy-2-butene, 1,4-dihydroxy-2-butene, and vinylene carbonate.

Examples thereof further include monomers containing a polyoxyalkylene group, such as polyoxyethylene(meth)allyl ether, polyoxyethylene(meth)acrylamide, polyoxypropylene (meth)acrylamide, polyoxyethylene(meth)acrylate, polyoxypropylene(meth)acrylate, polyoxyethylene(1-(meth) acrylamido-1,1-dimethylpropyl)ester, polyoxyethylene vinyl ether, polyoxypropylene vinyl ether, polyoxyethylene allylamine, polyoxypropylene allylamine, polyoxyethylene vinylamine, and polyoxypropylene vinylamine, and monomers containing a cationic group, such as N-acrylamidomethyltrimethylammonium chloride, N-acrylamidoethyltrimethylammonium chloride, N-acrylamidopropyltrimethylammonium chloride, 2-acryloxyethyltrimethylammonium chloride, 2-methacryloxyethylmethylammonium chloride, 2-hydroxy-3-methacryloyloxypropyltrimethylammonium chloride, allyltrimethylammonium chloride, methallyltrimethylammonium chloride, 3-butenetrimethylammonium chloride, dimethyldiallylammonium chloride, and diethyldiallylammonium chloride.

The amount of such a comonomer to be introduced cannot be unconditionally specified since the amount thereof varies depending on the kind of the monomer. However, the amount thereof is usually up to 10% by mole, especially up to 5% by mole, based on all the monomer units. Tho large amounts of the comonomer introduced are undesirable because there are cases where this copolymer has impaired water solubility or has reduced compatibility with the crosslinking agent.

It is also possible to use a copolymer which is produced by polymerizing or copolymerizing a vinyl ester monomer and other monomer(s) at a higher polymerization temperature to thereby form bonds of different kinds in an increased amount as compared with the 1,3-bonds which are mainly formed, thereby forming a PVA main chain that contains 1,2-diol bonds in an amount of about 1.6-3.5% by mole.

For introducing acetoacetyl groups into any of the PVA-based resins obtained by saponifying polymers and copolymers of such vinyl ester monomers, by reacting the resins with diketene, use may be made of a method in which the PVA-based resin is directly reacted with gaseous or liquid diketene. Alternatively, use may be made, for example, of: a method in which the PVA-based resin is caused to adsorb or occlude an organic acid beforehand and gaseous or liquid diketene is thereafter sprayed on and reacted with the PVA-based resin in an inert gas atmosphere; or a method in which a mixture of an organic acid and liquid diketene is sprayed on and reacted with the PVA-base resin.

With respect to reactors for performing the reaction, a reactor which is capable of heating and is equipped with a stirrer suffices. For example, use can be made of a kneader, Henschel mixer, ribbon blender, or any of other various blenders and stirring/drying devices.

The average degree of polymerization of the AA-modified PVA-based resin to be thus obtained may be suitably selected in accordance with applications thereof. However, AA-modified PVA-based resins suitable for use have an average degree of polymerization of usually 300-4,000, especially 400-3,500, more preferably 500-3,000. In case where the average degree of polymerization thereof is too low, there is a tendency that sufficient water resistance is not obtained or a sufficiently high crosslinking rate is not obtained. Conversely, in case where the average degree of polymerization thereof is too high, there is a tendency that in cases when this resin is used as an aqueous solution, this aqueous solution has too high a viscosity and is difficult to use in various steps, for example, difficult to apply to substrates.

The degree of saponification of the AA-modified PVA-based resin which is suitable for use in the invention is usually 80% by mole or higher, preferably 85% by mole or higher, especially 90% by mole or higher. In case where the degree of saponification thereof is too low, there is a tendency that it is difficult to obtain an aqueous solution thereof or that the aqueous solution has reduced stability or gives a crosslinked polymer having insufficient water resistance. Incidentally, the average degree of polymerization and the degree of saponification are determined in accordance with JIS K6726.

The acetoacetyl group content (hereinafter referred to as "degree of AA modification") of the AA-modified PVA-based resin which can be generally used extensively is usually 0.1-20% by mole, preferably 0.2-15% by mole, especially 0.3-10% by mole. In case where the content thereof is too low, there is a tendency that water resistance is insufficient or a sufficiently high erosslinking rate is not obtained. Conversely, in case where the content thereof is too high, there is a tendency that this resin has reduced water solubility or the aqueous solution has reduced stability.

In the invention, an AA-modified PVA-based resin having an average length of successive hydroxyl-group units of 10 or longer is usually used. An AA-modified PVA-based resin having an average length of successive hydroxyl-group units of 15 or longer is more suitable for use therein. In case where the length of successive hydroxyl-group units is too short, there is a tendency that the product of crosslinking reaction to be obtained has reduced water resistance.

The "average length of successive hydroxyl-group units" [I(OH)] is a value determined, through calculation using the following equation, from the absorption intensity proportions of absorptions attributable to methylene carbon moieties and appearing in the range of 38-46 ppm in $^{13}$C-NMR analysis (solvent: $D_2O$) in which 3-(trimethylsilyl)propionic-2,2,3,3-4d-acid sodium salt is used as an internal reference [absorption by (OH, OH) dyad=absorption having a peak top between 43 and 46 ppm; absorption by (OH, OR) dyad=absorption having a peak top between 41 and 43 ppm; and absorption by (OR, OR) dyad=absorption having a peak top between 38 and 41 ppm]

$$I(OH)=[2(OH, OH)+(OH, OR)]/(OH, OR)$$

(The absorption intensity proportions of (OH, OR) and (OH, OH) are each calculated in terms of molar proportion.)

This average length of successive hydroxyl-group units and a method for determination thereof are described in detail in "Poval" (published by Kobunshi Kanko-kai; page 248, 1981) and *Macromolecules*, Vol. 10, p. 532 (1977).

Methods for controlling the average length of successive hydroxyl-group units of an AA-modified PVA-based resin are not particularly limited. It is, however, preferable that in the step of saponifying polyvinyl acetate or the like when producing the PVA-based resin to be used as a starting material, the alkali saponification should be conducted in the presence of a solvent having a permittivity at 20° C. of 32 or less. The saponification is conducted at a permittivity of usually 6-28, preferably 12-25. In case where the permittivity is too high, there is a tendency that the residual acetic acid groups in the PVA-based resin have reduced block character regarding the arrangement thereof and the resultant AA-modified PVA-based resin has a shortened length of successive hydroxyl-group units.

Examples of the solvent having a permittivity at 20° C. of 32 or less include methanol (31.2), methyl acetate/methanol 1/3 (27.1), methyl acetate/methanol=1/1 (21.0), methyl acetate/methanol=3/1 (13.9), methyl acetate (7.03), isopropyl acetate (6.3), trichloroethylene (3.42), xylene (2.37), toluene (2.38), benzene (2.28), and acetone (21.4). Preferred of these are the methyl acetate/methanol mixed solvents.

In the invention, it is preferable that all the PVA-based resin(s) should be one or more AA-modified PVA-based resins. However, a PVA-based resin which is not an AA-modified PVA-based resin may have, been used in combination with one or more AA-modified PVA-based resins, and it is preferable that the content thereof should be usually 20% by weight or less, especially 10% by weight or less.

Examples of such various PVA-based resins which are not AA-modified PVA-based resins include unmodified PVA and various modified PVA resins. For example, use can be made of a product of saponification of a copolymer of a vinyl ester monomer with a monomer having copolymerizability with the vinyl ester monomer. Examples of the copolymerizable monomer include olefins such as ethylene, propylene, isobutylene, α-octene, α-dodecene, and α-octadecene, hydroxyl-containing α-olefins such as 3-buten-1-ol, 4-penten-1-ol, 5-hexen-1-ol, and 3,4-dihydroxy-1-butene and derivatives thereof such as acylation products, unsaturated acids such as acrylic acid, methacrylic acid, crotonic acid, maleic acid, maleic anhydride, itaconic acid, and undecylenic acid and salts, monoesters, or dialkyl esters thereof; nitriles such as acrylonitrile and methacrylonitrile, amides such as diacetone acrylamide, acrylamide, and methacrylamide, olefinsulfonic acids such as ethylenesulfonic acid, allylsulfonic acid, and methallylsulfonic acid and salts thereof, alkylvinyl ethers, vinyl compounds such as dimethylallyl vinyl ketone, N-vinylpyrrolidone, vinyl chloride, vinylethylene carbonate, 2,2-dialkyl-4-vinyl-1,3-dioxolanes, and glycerin monoallyl ether, substituted vinyl acetates such as isopropenyl acetate and 1-methoxyvinyl acetate, vinylidene chloride, 1,4-diacetoxy-2-butene, 1,4-dihydroxy-2-butene, and vinylene carbonate.

Some of the following substances may remain in the AA-modified PVA-based resin according to the invention: alkali metal acetates, e.g., sodium acetate, which were used in production steps or yielded as by-products in the steps (mainly derived from, for example, products of reactions between an alkali metal hydroxide used as a saponification catalyst and the acetic acid yielded by the saponification of polyvinyl acetate); organic acids such as acetic acid (derived from, for example, the organic acid which was occluded in PVA in preparation for reaction with diketene when acetoacetic acid ester groups were introduced into the PVA-based resin); and organic solvents such as methanol and methyl acetate (derived from, for example, a reaction solvent for the PVA-based resin or a cleaning solvent used during production of the AA-modified PVA-based resin)

The AA-modified PVA-based resin thus obtained is crosslinked with the crosslinking agent of the invention, thereby obtaining a crosslinked polymer. This crosslinked polymer is one obtained by reacting the AA-modified PVA-based resin with the alkylhydrazide compound as described above. The reaction between the acetoacetyl groups and the crosslinking agent of the invention is presumed to be caused by the nucleophilic addition of the hydrazide groups to the carbonyl groups of the acetoacetyl groups, and the crosslinked structure portions are thought to be represented by the following structural formula (2).

(Crosslinked Structure Involving AA Groups and Alkylhydrazide Groups)

[Chem. 9]

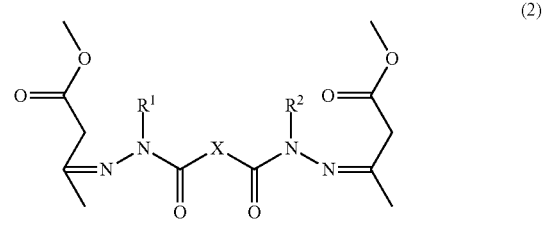

(2)

In formula (2), $R^1$, $R^2$, and X have the same meanings as in formula (1a).

In this crosslinking reaction, the proportion of the AA-modified PVA-based resin to the crosslinking agent, which includes the alkylhydrazide-group-containing compound as an effective component, is not particularly limited. However, a suitable range of the amount of the crosslinking agent to be used per 100 parts by weight of the AA-modified PVA-based resin is usually 0.1-200 parts by weight, preferably 0.5-100 parts by weight, especially 1-50 parts by weight. Meanwhile, the molar ratio of the amount of alkylhydrazide groups in the crosslinking agent (X) to the total amount of AA groups in the AA-modified. PVA-based resin (Y), X/Y, is in the range of usually 0.01-50, preferably 0.05-20, especially 0.1-10. When the amount of the alkylhydrazide groups is too small, there are cases where the resultant crosslinked polymer has insufficient water resistance. Conversely, when the amount thereof is too large, there are cases where the mixed aqueous solution is prone to increase in viscosity depending on the use environment, etc., resulting in a shortened pot life.

[DAAA-PVA-Based Resin and Crosslinked Polymer Therefrom]

Next, a crosslinked polymer obtained from the crosslinking agent of the invention and a PVA-based resin having a diacetone acrylamide structural unit (DAAA-PVA-based resin) is explained, this crosslinked polymer being a preferred mode of use of the crosslinking agent of the invention.

First, the DAAA-PVA-based resin is explained in detail.

The DAAA-PVA-based resin to be used in the invention is a PVA-based resin into which one or more diacetone acrylamide structural units have been introduced. For obtaining this DAAA-PVA-based resin, a method is preferably used in which a copolymer of a vinyl ester monomer and diacetone acrylamide is saponified.

Examples of the vinyl ester monomer to be subjected to the copolymerization include the same vinyl ester monomers as those usable for producing the AA-modified PVA-based resin. Preferred of these is vinyl acetate.

The copolymerization of such a vinyl ester monomer with diacetone acrylamide is not particularly limited, and use can be made of a known method such as bulk polymerization, solution polymerization, suspension polymerization, dispersion polymerization, or emulsion polymerization. Usually, solution polymerization is performed.

Examples of solvents usable in the copolymerization usually include lower alcohols such as methanol, ethanol, isopropyl alcohol, n-propanol, and butanol and ketones such as acetone and methyl ethyl ketone. Methanol is suitable for industrial use.

A polymerization catalyst is used for the copolymerization. Examples of the polymerization catalyst include known radical polymerization catalysts such as azobisisobutyronitrile, acetyl peroxide, benzoyl peroxide, and lauryl peroxide and low-temperature-active radical polymerization catalysts such as azobisdiethylvaleronitrile and azobismethoxydimethylvaleronitrile.

The copolymerization reaction may be performed at a reaction temperature of about 30° C. to the boiling point, depending on the solvent used and the pressure. More specifically, the reaction may be performed at a temperature in the range of 35-150° C., preferably 40-75° C.

The copolymer obtained is subsequently saponified. In preparation for the saponification, the copolymer obtained above is dissolved in a solvent such as an alcohol. This dissolved copolymer is saponified using an alkali catalyst or an acid catalyst. Representative examples of the solvent include methanol, ethanol, propanol, and tert-butanol. However, it is especially preferred to use methanol. Examples of the catalyst to be used in the saponification include alkali catalysts such as the hydroxides or alcoholates of alkali metals, e.g., sodium hydroxide, potassium hydroxide, sodium methylate, sodium ethylate, potassium methylate, and lithium methylate, and acid catalysts such as sulfuric acid, hydrochloric acid, nitric acid, methanesulfonic acid, zeolites, and cation-exchange resins.

The DAAA-PVA-based resin to be used in the invention may be one obtained by copolymerization with a monomer copolymerizable with the vinyl ester monomer or diacetone acrylamide, so long as the effects of the invention are not lessened thereby. Examples of this comonomer include the comonomers used when producing the PVA to be used as a starting material for the AA-modified PVA-based resin.

It is preferable that the average degree of polymerization (determined in accordance with JIS K6726) of the DAAA-PVA-based resin thus obtained should be 300-4,000, preferably 400-3,500, especially 500-3,000. When the average degree of polymerization thereof is too low there are cases where sufficient water resistance is not obtained or a sufficiently high crosslinking rate is not obtained. Conversely, when the degree of polymerization thereof is too high, there are cases where this resin gives an aqueous solution which has so high a viscosity that it is difficult to apply the solution to substrates or to use the solution in various steps. Such too low or too high degrees of polymerization are hence undesirable.

It is preferable that the degree of saponification of the DAAA-PVA-based resin according to the invention should be 80% by mole or higher, preferably 85% by mole or higher, especially 90% by mole or higher. Too low degrees of saponification thereof are undesirable because there are cases where this resin has reduced water solubility.

It is preferable that the content of diacetone acrylamide structural units in the DAAA-PVA-based resin according to the invention should be 0.1-20% by mole, preferably 0.2-15% by mole, especially 0.3-10% by mole. When the content thereof is too low, there are cases where sufficient water resistance is not obtained or a sufficiently high crosslinking rate is not obtained. Conversely, when the content thereof is too high, there are cases where this resin has reduced water solubility or the aqueous solution thereof has reduced stability. Such too low or too high contents of the units are hence undesirable.

The DAAA-PVA-based resin thus obtained is crosslinked with the crosslinking agent of the invention, thereby obtaining a crosslinked polymer. This crosslinked polymer is one obtained by reacting the DAAA-PVA-based resin with the compound containing alkylhydrazide groups. The crosslinking reaction with diacetone acrylamide structural units is presumed to be shown by the following structural formula (3).

(Cross Linked Structure Involving DAAA Structural Units and Alkylhydrazide Groups)

[Chem. 10]

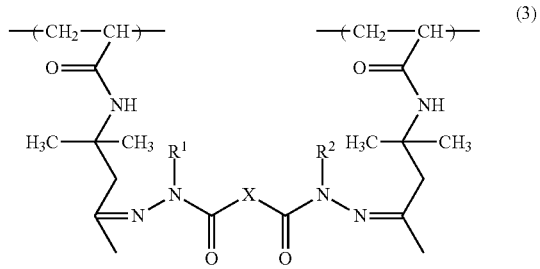

In formula (3), $R^1$, $R^2$, and X have the same meanings as in formula (1a).

In this crosslinking reaction, the proportion of the DAAA-PVA-based resin to the crosslinking agent, which includes the alkylhydrazide-group-containing compound as an effective component, is not particularly limited. However, a suitable range of the amount of the crosslinking agent to be used per 100 parts by weight of the DAAA-PVA-based resin is usually 0.1-200 parts by weight, preferably 0.5-100 parts by weight, especially 1-50 parts by weight. Meanwhile, the molar ratio of the amount of alkylhydrazide groups in the crosslinking agent (X) to the total amount of DAAA structural units in the DAAA-PVA-based resin (Y), X/Y, is in the range of usually 0.01-50, preferably 0.05-20, especially 0.1-10. When the amount of the alkylhydrazide groups is too small, there are cases where the resultant crosslinked polymer has insufficient water resistance. Conversely, when the amount thereof is too large, there are cases where the mixed aqueous solution is prone to increase in viscosity depending on the use environment, etc., resulting in a shortened pot life.

EXAMPLES

The present invention will be explained below by reference to Examples, but the invention should not be construed as being limited to the following Examples unless the invention departs from the spirit thereof.

In the following Examples and Comparative Examples, "parts" and "%" are by weight unless otherwise indicated.

Example 1

[Production of AA-Modified PVA (A1)]

Into a kneader was introduced 3,200 parts of a PVA-based resin having a degree of saponification of 97.7% by mole, an average degree of polymerization (determined in accordance with ITS K6726) of 2,400, and a sodium acetate content of 0.03%. Thereinto were introduced 960 parts of acetic acid and 45 parts of water to swell the resin. While stirring the contents at a rotation speed of 20 rpm, the contents were heated to 80° C. and, at a lowered temperature of 50° C., 390 parts of diketene was then added dropwise thereto over 4 hours and reacted for further 1 hour. After completion of the reaction, the solid matter was washed with methanol and then dried at 70° C. for 6 hours to obtain an AA-modified PVA-based resin (A1). This AA-modified PVA-based resin (A1) had a degree of AA modification of 4.0% by mole, and the degree of saponification and average degree of polymerization thereof were the same as those of the PVA-based resin used.

[Production of Crosslinking Agent Represented by the Following General Formula (4)]

(Synthesis of Adipic Acid Chloride)

The atmosphere in a reactor equipped with a stirrer, dropping funnel, reflux condenser, and three-way stop cock was replaced with nitrogen. Thereinto were introduced 77.6 g of adipic acid, several drops of pyridine, and 1,000 mL of dichloromethane to dissolve the solid. Thereto was added dropwise 252 g of thionyl chloride over 2 hours with cooling with ice. Thereafter, the mixture was heated with refluxing for 2 hours and then cooled to room temperature. The reflux condenser was replaced with a distillation device, and the internal pressure was reduced with heating at 50° C. using a diaphragm pump to remove the dichloromethane and the thionyl chloride, thereby obtaining 97.5 g of a light-yellow liquid.

(Synthesis of Compound of General Formula (4))

The atmosphere in a reactor equipped with a stirrer, dropping funnel, thermometer, and three-way stop cock was replaced with nitrogen. Thereafter, 196 g of methylhydrazine and 1,000 mL of dichloromethane were introduced thereinto to dissolve the solid. Subsequently, while maintaining an internal temperature of −5 to 0° C., the light-yellow liquid was added dropwise thereto over 4 hours. Thereafter, the mixture was stirred at room temperature for 22 hours. The resultant precipitate was taken out by filtration and washed with 2,250 mL of dichloromethane. The organic layers were collected and concentrated with heating at 80° C. under a reduced pressure using a rotary oil pump, thereby obtaining 121 g of a light-yellow liquid. To this light-yellow liquid was added 750 mL of chloroform. This mixture was stirred, and the insoluble matter was taken out by filtration and washed with 500 mL of chloroform. The filtrate and the washings were introduced into a column packed with silica gel, and 62.8 g of a white solid was obtained therefrom by chromatography.

[Chem. 11]

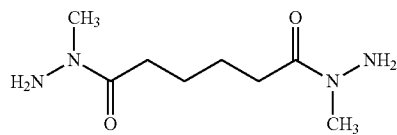

(4)

The white sold obtained (the compound of general formula (4)) was analyzed by $^1$H-NMR spectroscopy (using dpx400, manufactured by Bruker GmbH; solvent, d6-DMSO). The results thereof are as shown in FIG. 1, which included the following assignments.

4.664 ppm: hydrogen bonded to terminal amino group
3.344 ppm: water
2.978 ppm: hydrogen of methyl group bonded to nitrogen atom
2.508 ppm: DMSO
2.456 ppm: hydrogen of methylene group adjoining carbonyl group
1.463 ppm: hydrogen of methylene group adjoining methylene group adjoining carbonyl group This substance had a molecular weight of 202.

[Solubility]

The white solid obtained above was examined for solubility in 100 g of water at 23° C. As a result, the solubility thereof was found to be 150 g.

To 100 parts of a 5% by weight aqueous solution of the AA-modified PVA-based resin (A1) obtained above was added 5 parts of a 5% by weight aqueous solution of the compound represented by general formula (4) obtained above, as an alkylhydrazide-based compound (B). Immediately thereafter, 26 parts of the mixture was poured into a casting mold having dimensions of 10 cm×10 cm to produce a film. This cast film was allowed to stand at 23° C. and 50% RH for 3 days.

[Evaluation of Coloring]

Thereafter, the cast film was placed in a thermo-hygro static chamber of 40° C.×90% RH for 4 weeks in order to accelerate coloring, and was then subjected to a color measurement with a colorimeter. As the measuring device, spectrophotometric colorimeter CM-3600A (manufactured by Konica Minolta Sensing) was used. The measurement was made using illuminant D-6 by the transmission method. The film was evaluated on the basis of an average value for three specimens.

The a*, b*, and ΔE* values are shown in Table 1.

$$\Delta E^* \text{ value}=\sqrt{((L^*-L^{*0})^2+(a^*-a^{*0})^2+(b^*-b^{*0})^2)}$$

($L^{*0}$, $a^0$, and $b^{*0}$ are the results of a color measurement on a cast film formed from the aqueous solution of the AA-modified PVA-based resin only.

[Evaluation of Viscosity Stability]

Into a 225-mL bottle was introduced 150 parts of a 5% by weight aqueous solution of the AA-modified PVA-based resin (A1). After the temperature of the contents was adjusted to 40° C., 7.5 parts of a 5% by weight aqueous solution of the compound (B) represented by general formula (4) was added thereto. This bottle was shaken by hand to make 20 reciprocations over 30 seconds, thereby mixing the aqueous solutions.

The aqueous solution obtained was examined for viscosity using Brookfield viscometer DV-III with rotor No. 3 (rotation speed, 100 rpm), and the time period required for the viscosity to double was measured.

The results thereof are shown in Table 1.

Comparative Example 1

Aqueous solutions were obtained and evaluated in the same manners as in Example 1, except that adipic acid dihydrazide (ADH) was used as a crosslinking agent in place of the compound of general formula (4).

The results thereof are shown in Table 1.

Example 2

Aqueous solutions were obtained and evaluated in the same manners as in Example 1, except that a DAAA-PVA-based resin (average degree of polymerization. 1,700; degree of saponification, 99% by mole; content of diacetone acrylamide structural units, 4.5% by mole) was used in place of the AA-modified PVA-based resin.

The results thereof are shown in Table 1.

Comparative Example 2

Aqueous solutions were obtained and evaluated in the same manners as in Example 2, except that adipic acid dihydrazide (ADH) was used as a crosslinking agent in place of the compound of general formula (4).

The results thereof are shown in Table 1.

TABLE 1

|  | PVA-based resin | | Crosslinking agent | | Coloring | | | Viscosity stability |
|---|---|---|---|---|---|---|---|---|
|  | Modified kind | Degree of modification (mol %) | Kind | Solubility (g) | a* value | b* value | ΔE* | Gel time |
| Example 1 | AA-modified PVA | 4 | formula (4) | 150 | −0.1 | 0.6 | 0.3 | 19 hr |
| Comparative Example 1 | AA-modified PVA | 4 | ADH | 12.5 | −0.5 | 3.3 | 3.5 | 5 min |
| Example 2 | DAAA-PVA | 4.5 | formula (4) | 150 | 0.1 | 0.9 | 0.8 | did not gel |
| Comparative Example 2 | DAAA-PVA | 4.5 | ADH | 12.5 | 1.2 | 0.5 | 2.1 | 15 hr |

Examples 1 and 2, in which the crosslinking agent of the invention was used, attained small values of ΔE* as compared with Comparative Examples 1 and 2, in which ADH was used, and were able to inhibit the films from yellowing or becoming reddish. In particular, the crosslinking agent is effective in preventing the AA-modified PVA from yellowing (b* value), and is effective in preventing the DAAA-PVA from becoming reddish (a* value). With respect to viscosity, the solutions of the Examples had longer gel times than the ADH-containing solutions, and showed stable viscosity over a prolonged period.

While the invention has been described in detail and with reference to specific embodiments thereof, it will be apparent to one skilled in the art that various changes and modifications can be made therein without departing from the spirit and scope thereof. This application is based on a Japanese patent application filed on Oct. 9, 2013 (Application No. 2013-211979), the contents thereof being incorporated herein by reference.

INDUSTRIAL APPLICABILITY

The crosslinking agent of the invention is less apt to cause coloring with the lapse of time and is excellent also in terms of viscosity stability. The crosslinking agent hence is especially suitable for use in coating layers to be formed on various substrates, and in paper applications, etc.

The invention claimed is:

1. A crosslinkable composition comprising:
a compound which contains two or more alkylhydrazide groups represented by the following formula (1):

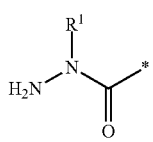

(1)

in which $R^1$ represents an alkyl group having 1-10 carbon atoms, and the symbol * is a linking bond; and
a polymer having carbonyl groups.

2. The crosslinkable composition according to claim 1, wherein the compound has a solubility in 100 g of water of 50-500 g at 23° C.

3. The crosslinkable composition according to claim 1, wherein the compound has a molecular weight of 150-3,000.

4. The crosslinkable composition according to claim 1, wherein the compound is a dicarboxylic acid bis(1-alkylhydrazide) compound represented by the following formula (1a):

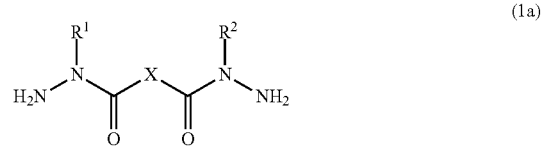

(1a)

in which $R^1$ and $R^2$ each independently represent an alkyl group having 1-10 carbon atoms, and X represents a single bond or an alkylene chain having 1-10 carbon atoms.

5. The crosslinkable composition according to claim 1, wherein the polymer is a polyvinyl alcohol-based resin.

6. A crosslinked polymer produced by crosslinking the crosslinkable composition according to claim 5.

7. A method for preparing a crosslinkable composition comprising combining
a compound which contains two or more alkylhydrazide groups represented by the following formula (1):

(1)

in which $R^1$ represents an alkyl group having 1-10 carbon atoms, and the symbol * is a linking bond with a polymer comprising carbonyl groups.

* * * * *